(12) United States Patent
Kertz (10) Patent No.: US 8,372,632 B2
(45) Date of Patent: Feb. 12, 2013

(54) METHOD AND APPARATUS FOR $CO_2$ SEQUESTRATION

(76) Inventor: Malcolm Glen Kertz, El Paso, TX (US)

( * ) Notice: Subject to any disclaimer, the term of this patent is extended or adjusted under 35 U.S.C. 154(b) by 1194 days.

(21) Appl. No.: 11/762,295

(22) Filed: Jun. 13, 2007

(65) Prior Publication Data

US 2007/0289206 A1  Dec. 20, 2007

Related U.S. Application Data

(60) Provisional application No. 60/804,763, filed on Jun. 14, 2006, provisional application No. 60/892,331, filed on Mar. 1, 2007.

(51) Int. Cl.
| | |
|---|---|
| *A01G 7/00* | (2006.01) |
| *A01H 13/00* | (2006.01) |
| *C12M 1/36* | (2006.01) |
| *C12M 1/38* | (2006.01) |
| *C12M 1/09* | (2006.01) |
| *C12M 1/00* | (2006.01) |
| *C12M 3/00* | (2006.01) |
| *C12M 1/24* | (2006.01) |
| *C12N 1/12* | (2006.01) |

(52) U.S. Cl. ............... 435/292.1; 435/257.1; 435/286.6; 435/286.7; 435/296.1; 435/304.1; 47/1.4; 47/17

(58) Field of Classification Search ............... 435/286.6, 435/286.7, 292.1, 296.1, 304.1, 257.1; 47/1.4, 47/17

See application file for complete search history.

(56) References Cited

U.S. PATENT DOCUMENTS

| | | | |
|---|---|---|---|
| 1,798,565 | A | 3/1931 | Trullinger |
| 2,312,221 | A | 2/1943 | Springman et al. |
| 3,224,143 | A | 12/1965 | Tew |
| 4,831,196 | A | 5/1989 | Buonicore et al. |
| 4,970,166 | A | 11/1990 | Mori |
| 5,476,787 | A | 12/1995 | Yokoyama et al. |
| 5,506,117 | A | 4/1996 | Andrews et al. |
| 5,534,417 | A | 7/1996 | Arad et al. |
| 5,614,378 | A | 3/1997 | Yang et al. |
| 5,707,868 | A | 1/1998 | Boulay et al. |

(Continued)

FOREIGN PATENT DOCUMENTS

| | | |
|---|---|---|
| CN | 1089991 A | 7/1994 |
| CN | 1201827 A | 12/1998 |

(Continued)

OTHER PUBLICATIONS

International Search Report and Written Opinion dated May 31, 2010 for Appl. PCT/US2009/045421; (5 p.).

(Continued)

*Primary Examiner* — Nathan Bowers
*Assistant Examiner* — Lydia Edward
(74) *Attorney, Agent, or Firm* — Conley Rose, P.C.

(57) ABSTRACT

A method and apparatus for sequestering $CO_2$ using algae comprises a plurality of vertically suspended bioreactors, each bioreactor being translucent and including a flow channel formed by a plurality of baffles. A culture tank contains a suspension of water and at least one algae and includes a plurality of gas jets for introducing a $CO_2$-containing gas into the suspension. The culture tank is in fluid communication with an inlet in each channel for flowing the suspension through the channel in the presence of light. A pump pumps the suspension into the channel inlet.

24 Claims, 6 Drawing Sheets

U.S. PATENT DOCUMENTS

| | | | |
|---|---|---|---|
| 5,846,816 A * | 12/1998 | Forth | 435/292.1 |
| 5,981,271 A | 11/1999 | Doucha et al. | |
| 6,509,188 B1 * | 1/2003 | Trosch et al. | 435/292.1 |
| 6,571,735 B1 | 6/2003 | Wilkinson | |
| 6,667,171 B2 | 12/2003 | Bayless et al. | |
| 2005/0260553 A1 * | 11/2005 | Berzin | 435/3 |
| 2007/0048848 A1 | 3/2007 | Sears | |
| 2007/0048859 A1 | 3/2007 | Sears | |
| 2008/0086938 A1 | 4/2008 | Hazlebeck et al. | |
| 2008/0087165 A1 | 4/2008 | Wright et al. | |

FOREIGN PATENT DOCUMENTS

| | | |
|---|---|---|
| DE | 20017229 | 3/2002 |
| EP | 0576870 A2 | 1/1994 |
| EP | 0935991 A1 | 8/1999 |
| GB | 2235210 | 2/1991 |
| JP | 5236935 A | 9/1993 |
| WO | 2005121309 A1 | 12/2005 |
| WO | 2007098150 | 8/2007 |
| WO | 2007147028 | 12/2007 |

OTHER PUBLICATIONS

Examination Report and Novelty Search dated Mar. 19, 2009 for Appl. No. GCC/P/2007/8509; (9 p.).

International Search Report for PCT Appl. No. PCT/US2007-071165 dated Dec. 14, 2007 (7 p.).

GCC/P/2007/8509 Examination Report dated Mar. 3, 2010 (5 p.) (2405-01805).

Malaysian Examination Report dated Mar. 31, 2011; Malaysian Application No. PI 20070930 (3 p.) (2405-01807).

Malaysian Response to Examination Report dated Mar. 31, 2011; Malaysian Application No. PI 20070930; Response filed Aug. 10, 2011 (6 p.) (2405-01807).

Panama Examination Report dated Jun. 5, 2008; Panamanian Application No. 87311 (3 p.) (2405-01808).

Panama Response to Examination Report dated Jun. 5, 2008; Response filed Mar. 23, 2009; Panamanian Application No. 87311 (7 p.) (2405-01808).

Chinese 2nd Office Action Dated Aug. 2, 2012; Chinese Application No. 200780022235.9 (2405-01812) (12 p.).

Office Action Dated Jun. 30, 2011; U.S. Appl. No. 12/128,294 (2405-01809) (17 p.).

Response to Office Action Dated Jun. 30, 2011; U.S. Appl. No. 12/128,294; Response Filed Nov. 1, 2011 (2405-01809) (14 p.).

Office Action Dated May 10, 2012; U.S. Appl. No. 12/128,294 (2405-01809) (19 p.).

Response to Office Action Dated May 10, 2012; U.S. Appl. No. 12/128,294; Response Filed Sep. 10, 2012 (2405-01809) (16 p.).

European Search Report Dated Sep. 28, 2012; European Application No. 07798534.9 (2405-01813) (5 p.).

* cited by examiner

METHOD AND APPARATUS FOR $CO_2$ SEQUESTRATION

CROSS-REFERENCE TO RELATED APPLICATIONS

This application claims benefit of U.S. provisional application Ser. No. 60/804,763 filed Jun. 14, 2006, and entitled "Method and Apparatus for $CO_2$ Sequestration," and U.S. provisional application Ser. No. 60/892,331 filed Mar. 1, 2007, both hereby incorporated herein by reference.

STATEMENT REGARDING FEDERALLY SPONSORED RESEARCH OR DEVELOPMENT

Not applicable.

BACKGROUND

1. Field of the Invention

This invention relates to generally to the field of $CO_2$ sequestration and more specifically to an apparatus and methods for sequestering $CO_2$ using algae.

2. Background of the Invention

Increasing global levels of carbon dioxide ($CO_2$) has been a worldwide concern for some time. Measured in terms of volume, there were about 280 parts of $CO_2$ in every million parts of air at the beginning of the Industrial Revolution, and today there are 360 parts per million (ppm), a 30 percent increase. The annual increase is 2 ppm, and rising. If present trends continue, the concentration of $CO_2$ in the atmosphere will double to about 700 ppm in the latter half of the 21st century. Many scientists now believe that most of the global warming observed over the past 50 years can be attributed to this increase in carbon dioxide from human activities.

It is well known that green plants uptake $CO_2$ through photosynthesis. Photosynthesis converts the renewable energy of sunlight into energy that living creatures can use. In the presence of chlorophyll, plants use sunlight to convert $CO_2$ and water into carbohydrates that, directly or indirectly, supply almost all animal and human needs for food; oxygen and some water are released as by-products of this process. The principal factors affecting the rate of photosynthesis are a favorable temperature, level of light intensity, and availability of carbon dioxide. Most green plants respond quite favorably to concentrations of $CO_2$ well above current atmospheric levels.

While there are a number of ways to increase carbon dioxide uptake in biological systems such as plants, it has proven difficult to do so in a cost effective method. Various strains of algae offer the fastest $CO_2$ uptake. Ocean based enrichment programs are invasive and may lead to more problems than they solve. Specifically they tend to grow weed forms of algae and can damage or destroy entire ecosystems. Additionally, there is no way to harvest the algae produced by such means.

Land-based algae systems are very effective in capturing $CO_2$, but are limited by available land space and cost. In an open passive or batch system, it is only possible to produce approximately 150 metric tons of dry biomass from algae per hectare per year. Using these figures, it would require over 200 hectares of open land to capture the output from a 1000-megawatt gas turbine power plant, not even taking into consideration weather and water availability. Critical to the production of large amounts of algae is the presence of light. Algae uses light to convert $CO_2$ into sugars, i.e. photosynthesis. Unfortunately, light only penetrates a few centimeters into an active culture of algae. As the algae organisms multiply and the culture density increases, the degree of light penetration decreases. Some research has utilized the use of fiber optics, which has thus far been prohibitively expensive and ineffective.

Consequently, there is a need for an apparatus and methods for sequestering $CO_2$ using algae, which exposes the algae to a sufficient amount of light in a cost-effective manner.

BRIEF SUMMARY

An apparatus and method for sequestering and removing $CO_2$ from a gas using algae are described herein. The disclosed apparatus and methods provide a continuous process for the sequestration of $CO_2$ using one or more bioreactors, each having baffled channels that allow the algae to react with $CO_2$. Each bioreactor is formed from a transparent or translucent polymeric material that forms a channel therethrough that is inexpensive as well as easily manufactured. In addition, the channel through the transparent or translucent polymeric material provides a large surface area for light exposure allowing greater exposure of the algae to light as well as flexibility in channel configurations.

In one embodiment, the apparatus for sequestering $CO_2$ comprises a culture tank containing a suspension of water and at least one type of algae. The culture tank comprises a plurality of gas jets for introducing a $CO_2$-containing gas into the suspension. The apparatus also comprises one or more bioreactors each forming a channel for the flow of the suspension therethrough, wherein each bioreactor comprises a plurality of baffles and an inlet. Each inlet is located preferably at the top of each bioreactor and is in fluid communication with the culture tank. Furthermore, the apparatus comprises a pump for pumping the suspension to the inlets at the top of the one or more bioreactors.

In another embodiment, a method of sequestering $CO_2$ comprises introducing a $CO_2$-containing gas into a culture tank filled with a suspension of water and at least one algae such that the $CO_2$ is dissolved in the suspension. The method further comprises flowing the suspension from the culture tank through a plurality of vertically suspended bioreactors by gravity flow, the plurality of bioreactors each having culture channels with a plurality of horizontal baffles. Moreover, the method comprises exposing the bioreactors to light. In addition, the method comprises converting the $CO_2$ into at least one organic compound by photosynthesis.

One of the many advantages of the disclosed methods and apparatus is the incorporation of a dynamic or continuous process rather than a batch process. The continuous process allows maximal exposure of light to a constantly moving stream of algae. Thus, when compared to batch systems, each algae organism will eventually be exposed to light as it continuously flows through the disclosed system.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

NOTATION AND NOMENCLATURE

Certain terms are used throughout the following description and claims to refer to particular system components. This document does not intend to distinguish between components that differ in name but not function. In the following discussion and in the claims, the terms "including" and "comprising" are used in an open-ended fashion, and thus should be interpreted to mean "including, but not limited to . . . ".

DETAILED DESCRIPTION OF THE PREFERRED EMBODIMENTS

Figure 1:
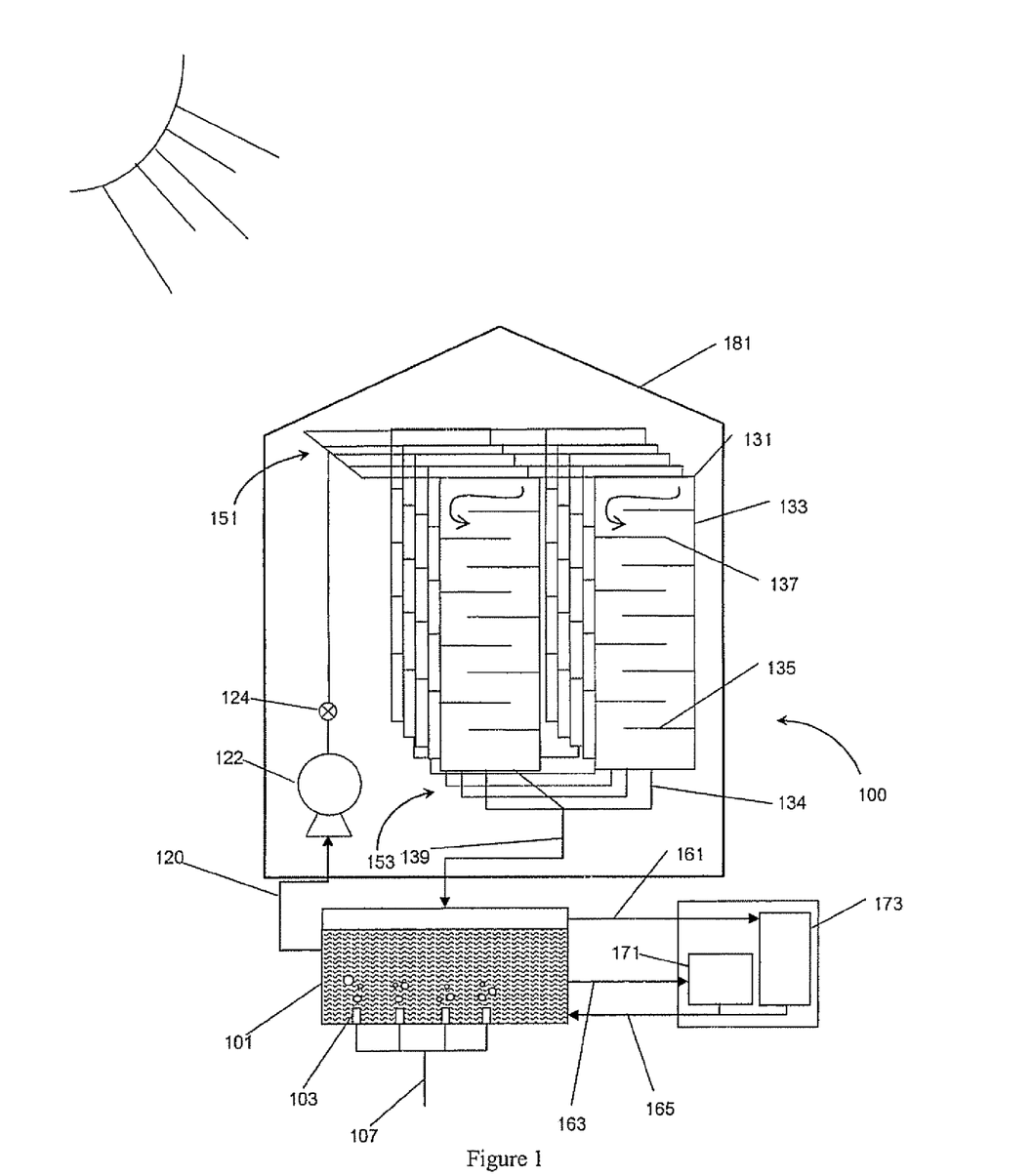
FIG. 1 illustrates a schematic of an apparatus for sequestering $CO_2$ using algae.

FIG. 1 illustrates an embodiment of an apparatus for sequestering $CO_2$ using algae. In this embodiment, the apparatus includes a culture tank 101, a pump 122, and one or more bioreactors 131. The culture tank 101, pump 122, and bioreactors 131 are all in fluid communication with each other and are all connected to each other via a plurality of conduits or lines.

The culture tank 101 is filled with a suspension of algae and water. Typically, culture tank 101 has a rectangular structure. However, culture tank 101 may be of any configuration, i.e. cylindrical, known to one of ordinary skill that is optimal for culturing algae. Culture tank 101 is made out of materials that are resistant to corrosion such as polymers or stainless steel. In a preferred embodiment, culture tank 101 is constructed out of plastic, plastic liner, treated metal, or combinations thereof. According to another embodiment, culture tank 101 is closed to the atmosphere such that apparatus 100 is a closed system. Having a closed system prevents contamination of the algae suspension as well as evaporation of the water. Thus, the only gas entering culture tank 101 is through gas jets 103. Moreover, all culture medium and fluids entering bioreactors 131 are preferably sterile to further prevent contamination. That is, the suspension is flowed through the bioreactors 131 under sterile conditions. As used herein, sterile conditions may refer to conditions known to those of ordinary skill in the art sufficient to maintain an aseptic environment free of contaminating germs or microorganisms.

Culture tank 101 also comprises at least one gas jet 103. The gas jets 103 introduce a $CO_2$-containing gas into culture tank 101. Gas jets 103 may comprise any type of suitable inlets such as valves, nozzles, or gas diffusers. In a preferred embodiment, the plurality of gas jets 103 comprise a plurality of gas diffusers. Gas diffusers break up the introduced gas into smaller, more soluble bubbles. According to another preferred embodiment, the plurality of gas jets 103 are located at the bottom of culture tank.

Any suitable algae may be cultured in the tank 101. In a preferred embodiment, the algae species, *Chlorella*, is used. Other examples of suitable algae species include, without limitation, red algae, brown algae, *Spirulina*, or combinations thereof. According to preferred embodiments, the algae species is preferably non-filamentous so as not to clog the apparatus. In an embodiment, the algae species is a single-cell algae species ranging from about 1 micron to about 15 microns.

Generally, water, i.e. tap water or distilled water, is used to culture the algae. In an embodiment, the water is sterile and free from all contaminants. Alternatively, saltwater may be used to culture saltwater species of algae. However, any appropriate culture mediums know to those of skill in the art may be used depending on the specific algae species. In other embodiments, a plurality of fish may be maintained in culture tank 101. The fish consume algae as well as produce nitrate in the form of feces. The fish feces are used to further nourish the algae. In further embodiments, culture tank 101 may include one or more feed inlets to introduce or provide additional nutrients to the algae. The one or more feed inlets may be coupled to one or more feed tanks filled with specific types of nutrients, minerals, mediums, or the like. In an embodiment, the one or more feed tanks may be disposed in series or in parallel to culture tank. Preferably, feed inlets and feed tanks are maintained under sterile conditions.

Figure 2:
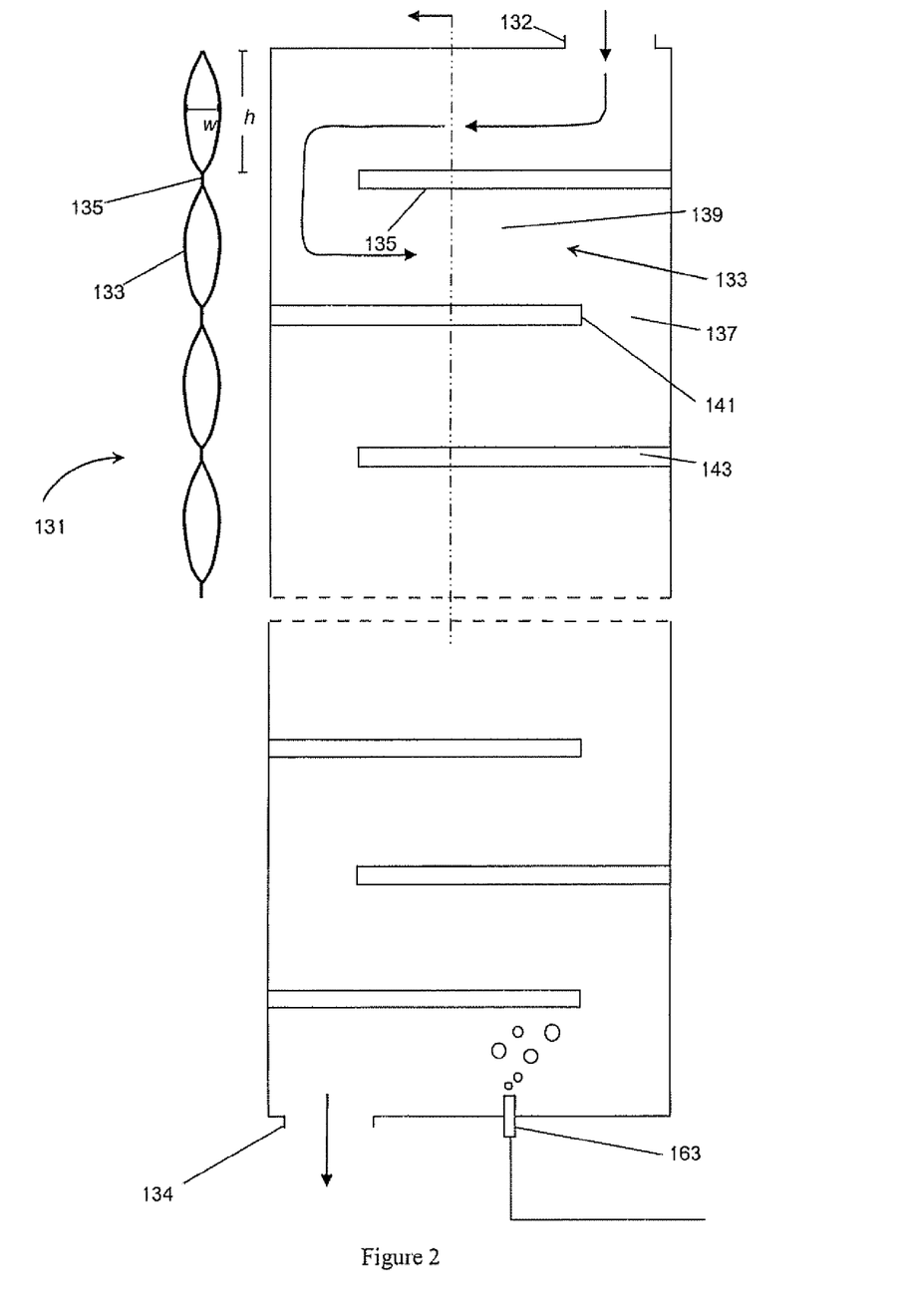
FIG. 2 illustrates a cross-sectional side-view and frontal view of a portion of an embodiment of a bioreactor culture channel.

A feed conduit 120 extends from the culture tank 101 to the pump 122. Pump 122 is any suitable device capable of pumping the suspension. Examples of suitable devices include without limitation, centrifugal pumps, impeller pumps, or rotary pumps. In one embodiment, feed conduit 120 additionally comprises an air inlet valve 124 allowing more $CO_2$-containing gas to saturate the algae suspension. Air inlet valve 124 allows gas to enter the feed conduit 120, but does not allow any of the algae suspension to escape. Thus, the algae suspension is constantly being supplied with carbon dioxide. Feed conduit 120 further extends from pump 122 to an inlet manifold 151. Inlet manifold 151 distributes the $CO_2$-enriched algae suspension to the inlets 132 of each bioreactor 131. The inlet 132 of each bioreactor 131 is preferably located on the top of each bioreactor 131 such that the algae suspension flows downward through the bioreactor as shown in FIG. 2.

The bioreactors 131 are generally constructed from any transparent or translucent polymeric material. In other words, a polymeric material that is permeable to light. Furthermore, the polymeric material is preferably a flexible material. A flexible material allows the bioreactor to compensate for different flow rates as well as being easier to handle. In some cases, the polymeric material may even possess elastic properties. Examples of suitable materials include without limitation, polypropylene, polystyrene, polypropylene-polyethylene copolymers, polyurethane, or combinations thereof. In a preferred embodiment, the bioreactors 131 are made of polyethylene. Any type of polyethylene may be used including high-density polyethylene or low-density polyethylene.

Furthermore, the polymeric material is UV treated to withstand repeated and extended exposure to light.

The thickness of the polymeric material is in the range of about 3 mm to about 10 mm, more preferably from about 4 mm to about 6 mm. The polymeric material preferably has a tensile strength capable of withstanding the weight of at least 50 gallons of water.

The polymeric material is typically produced in the form of a tube and is heat sealable. The tubular polymeric material is folded forming adjacent sides that are heat sealed to close the upper and lower ends of the tubular polymeric material and to form internal flow channels 133, hereinafter described in further detail. It should be appreciated that the bioreactors 131 may be made from two planar sheets of polymeric material that are heat sealed to seal the sides of the bioreactors 131.

According to a preferred embodiment, bioreactors 131 are substantially planar in configuration. In an exemplary embodiment, each bioreactor is about 10 ft tall and about 2 ft wide, alternatively about 10 ft tall and about 4 ft wide, alternatively about 10 ft tall and about 10 ft wide. However, in other embodiments, each bioreactor may range from about 4 feet wide to about 30 feet wide and from about 5 feet tall to about 20 feet tall. Moreover, the height:width ratio of each bioreactor may be any ratio. In embodiments, the height: width ratio of each bioreactor may range from about 10:1 to about 1:1. In addition, each bioreactor 131 may have different heights and widths in order to optimize light exposure to the circulating algae.

Flow channels 133 are formed by a plurality of baffles or partitions 135. Baffles 135 serve to maximize the residence time of the algae in each flow channel 133. The greater the residence time of the algae, the longer the algae in the bioreactor 131 is exposed to light. In embodiments, the residence time of the algae in bioreactors 131 may range from about 1 minute to about 60 minutes, alternatively from about 5 minutes to about 45 minutes, alternatively from about 10 minutes to about 15 minutes. In an embodiment, the baffles 135 may be created by heat-sealing the polymeric material at specific locations along adjacent sides of the material.

Baffles 135 define the flow channel 133 within each bioreactor 131. FIG. 2 shows a cross-section of channels 133 in a typical embodiment of a bioreactor 131. In FIG. 2, h refers to the height of each channel 133 (the space between each baffle 135) and w refers to the maximum width of each channel 133. Preferably, h is no more than about 3 inches. Additionally, in most embodiments, h is preferably no more than about 2 inches. The width, w, of each channel is set such that the algae flowing through each channel 133 receives sufficient light to survive. The weight of the suspension flowing through the bioreactor stretches the polymeric material causing the width w to be maintained at a minimum so as to allow the light passing through the polymeric material to reach all of the algae in the suspension flowing through the channels 133. This weight prevents the channels 133 from ballooning so as to increase the width w and prevent the light from reaching the algae flowing through the center of the channel 133.

Figure 4A:
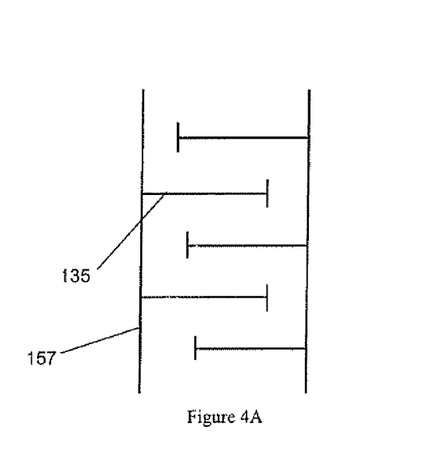
FIG. 4A illustrates an elevation view of a bioreactor with vertical baffles.

In certain embodiments, baffles 135 are arranged in an alternating horizontal configuration to form generally horizontal channels 139 and end channels 137. Each horizontal channel 139 has an open end 141 and a closed end 143. End channel 137 is formed around the open end 141 of an upper baffle 135 together with a closed end 143 of an adjacent lower baffle 135. Baffles 135 form a serpentine configuration of the channel 133. Each baffle end 141 creates turbulence in the algae suspension as it flows downward through the bioreactor 131. The turbulence creates vortexes at these ends 141, which allow for better mixing of the algae suspension. Additional baffles (FIG. 4A) may be configured in vertical orientations to the horizontally arranged baffles 135 to further increase residence time of the culture suspension.

Figure 3:
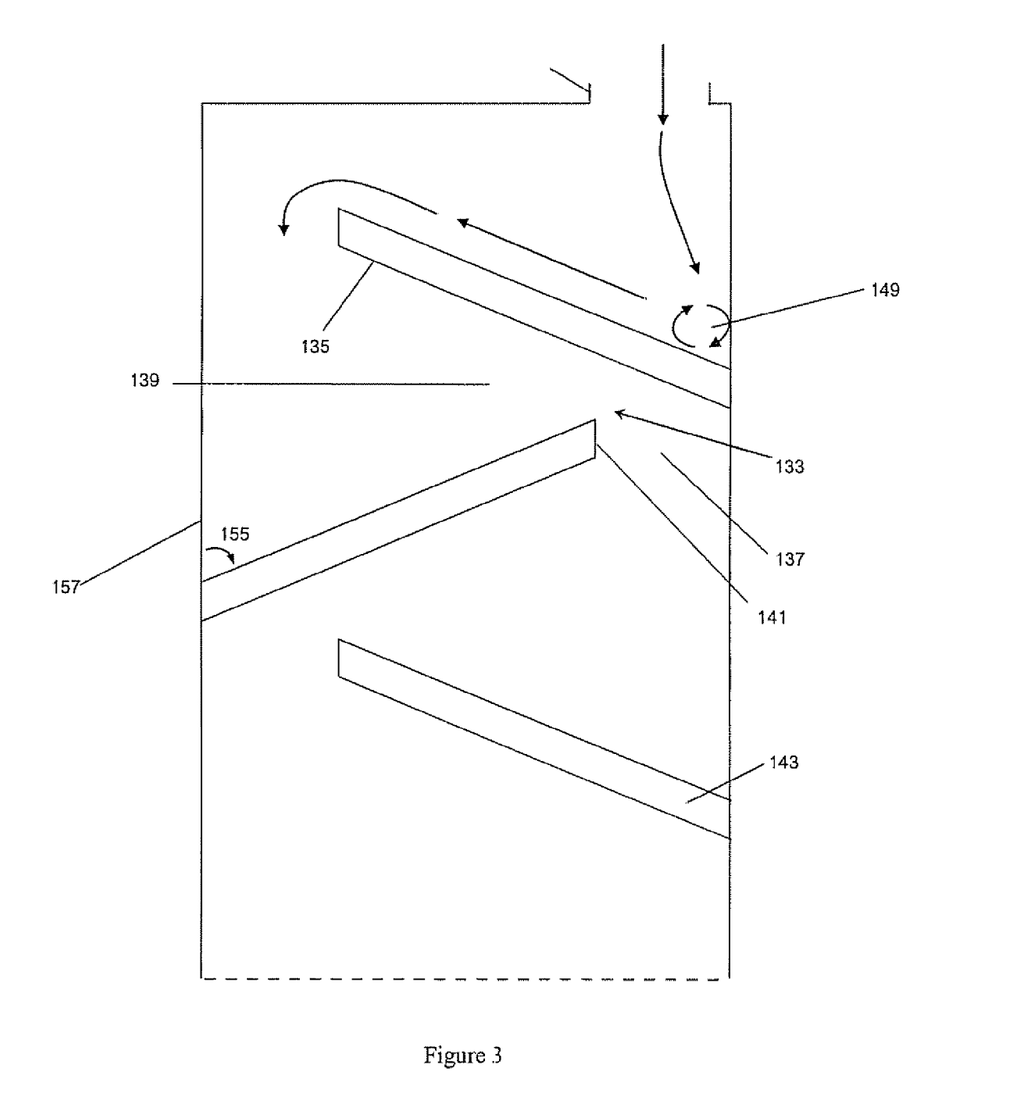
FIG. 3 illustrates another embodiment of a bioreactor culture channel.
Figure 4B:
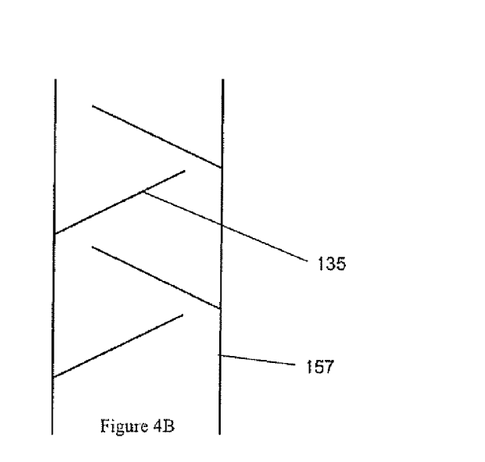
FIG. 4B illustrates an elevation view of an embodiment having upwardly angled baffles.
Figure 4C:
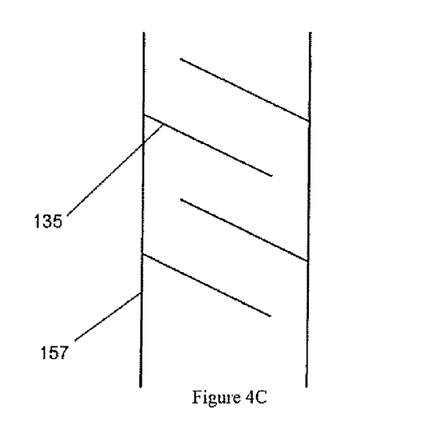
FIG. 4C illustrates an elevation view of an embodiment having upward and downward angled baffles in a parallel configuration.
Figure 4D:
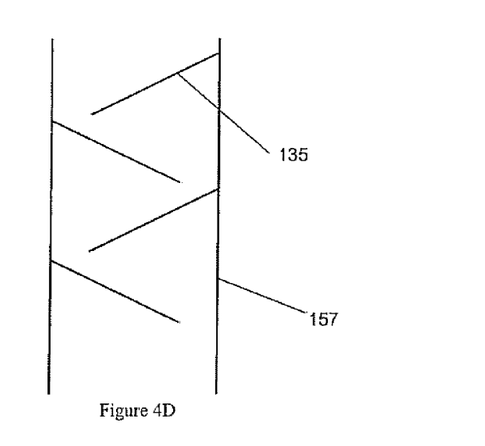
FIG. 4D illustrates an elevation view of an embodiment having all downward angled baffles.

Referring now to FIG. 3, in an additional embodiment, baffles 135 are angled upward to increase residence time of algae in bioreactor 131 as shown in FIG. 3. That is, each baffle 135 forms an upward acute angle 155 with the side 157 of bioreactor 131 toward the top of bioreactor 131. A corner 149 or pocket is formed at the intersection of each baffle 135 and side 157 of bioreactor 131. Corner 149 may cause the formation of vortexes in the circulating algae and culture medium. As algae flows through bioreactor 131, the algae may circulate or swirl temporarily in the vortices or mixing zones formed at each corner 149 thus, increasing exposure time of the algae in bioreactor 131 to light. In some embodiments, baffles 135 may be angled downwardly as shown in FIG. 4D. Thus, it is envisioned that baffles 135 may be angled at any suitable angle from the side 157 of bioreactor 131 ranging from about 30° to about 160°.

In general, each baffle 135 is angled at the same angle. However, in other embodiments, each baffle 135 may be angled at different angles to each other. FIGS. 4A-D illustrate various configurations of baffles 135 which may be incorporated into bioreactor 131. FIG. 4B shows an embodiment where baffles 135 are all upwardly angled. FIG. 4C shows an embodiment where baffles 135 are configured in an alternating upward and downward angled parallel arrangement. FIG. 4D shows an embodiment where baffles 135 are all downwardly angled. It is to be understood that the arrangement of baffles 135 are not limited by these embodiments, but may comprise an unlimited number of configurations to increase the sequestration of $CO_2$ by the algae. In embodiments with a plurality of bioreactors 131, each bioreactor may comprise a different baffle arrangement or configuration in order to optimize algae residence time.

Figure 5A:
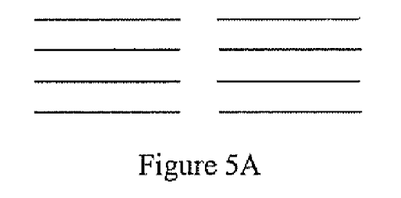
FIG. 5A illustrates a top view of a configuration of one or more bioreactors in a rectangular matrix formation.
Figure 5B:
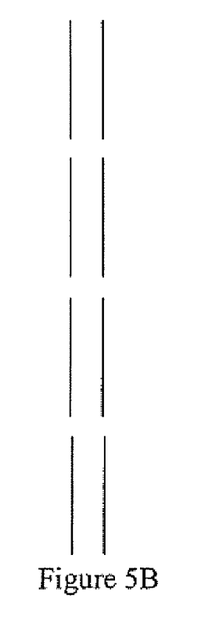
FIG. 5B illustrates a top view of configuration of one or more bioreactors in another rectangular matrix configuration.
Figure 5C:
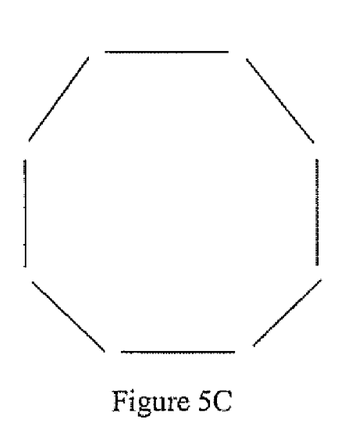
FIG. 5C illustrates a top view of a configuration of one or more bioreactors in a polygonal configuration.

According to preferred embodiments, the plurality of transparent bioreactors 131 are suspended or hung vertically. Bioreactors 131 may be hung in any suitable configuration. However, it is desirable for bioreactors 131 to be hung such that each channel 133 is exposed to the maximum amount of light. FIGS. 5A-C depict a schematic top view of the different variations at which the bioreactors 131 may be hung or suspended from a top-down view. FIG. 5A shows a typical embodiment in which the bioreactors are configured in a rectangular matrix formation. For example, in FIG. 5A, the matrix is two bioreactors wide and 6 bioreactors channels deep. FIG. 5B shows yet another embodiment in which the matrix is 6 bioreactors wide and two bioreactors deep. In embodiments where bioreactors are arranged in a matrix formation, the bioreactors 131 preferably are no more than 6 inches apart. FIG. 5C illustrates another embodiment in which the bioreactors are arranged in a polygonal configuration. Thus, the bioreactors provide nearly unlimited possibilities in configurations so as to maximize exposure of the culture medium to light.

In certain embodiments, bioreactors 131 are hung at different heights. Hanging bioreactors 131 at different heights changes the flow rate of the algae suspension through each bioreactor 131. It is believed that differing flow rates for each bioreactor 131 provides improved distribution of light to each bioreactor 131.

Referring now to FIG. 1, an outlet manifold 153 directs flow from the outlet 134 of each bioreactor 131. Typically, outlets 134 are located at the bottom of each bioreactor and lead to an outlet manifold 153. Outlet manifold 153 distributes the flow into an outlet conduit 139. Outlet conduit 139 recirculates the algae suspension back into culture tank 101.

Alternatively, each bioreactor 131 has an individual outlet conduit coupled to each outlet 134. Each outlet conduit then drains directly into culture tank. According to another embodiment, each bioreactor 131 includes a gas inlet 163 as seen in FIG. 2. Gas inlet 163 is typically disposed at the bottom or lower end of each bioreactor 131. However, gas inlet 163 may be disposed at any portion of bioreactor 131. In an embodiment, gas inlet 163 may be coupled to gas supply line 107. Furthermore, gas inlet 163 may include a valve for adjusting the flow of gas into bioreactor 131. The function of gas inlet 163 will be described in more detail below. In additional embodiments, outlet manifold 153 may have one or more vents to purge any excess oxygen present in the bioreactors. The one or more vents may comprise one or more purge valves. Furthermore, the one or more vents may vent excess oxygen in a manner such as to maintain sterile conditions in the bioreactors 131.

Figure 6:
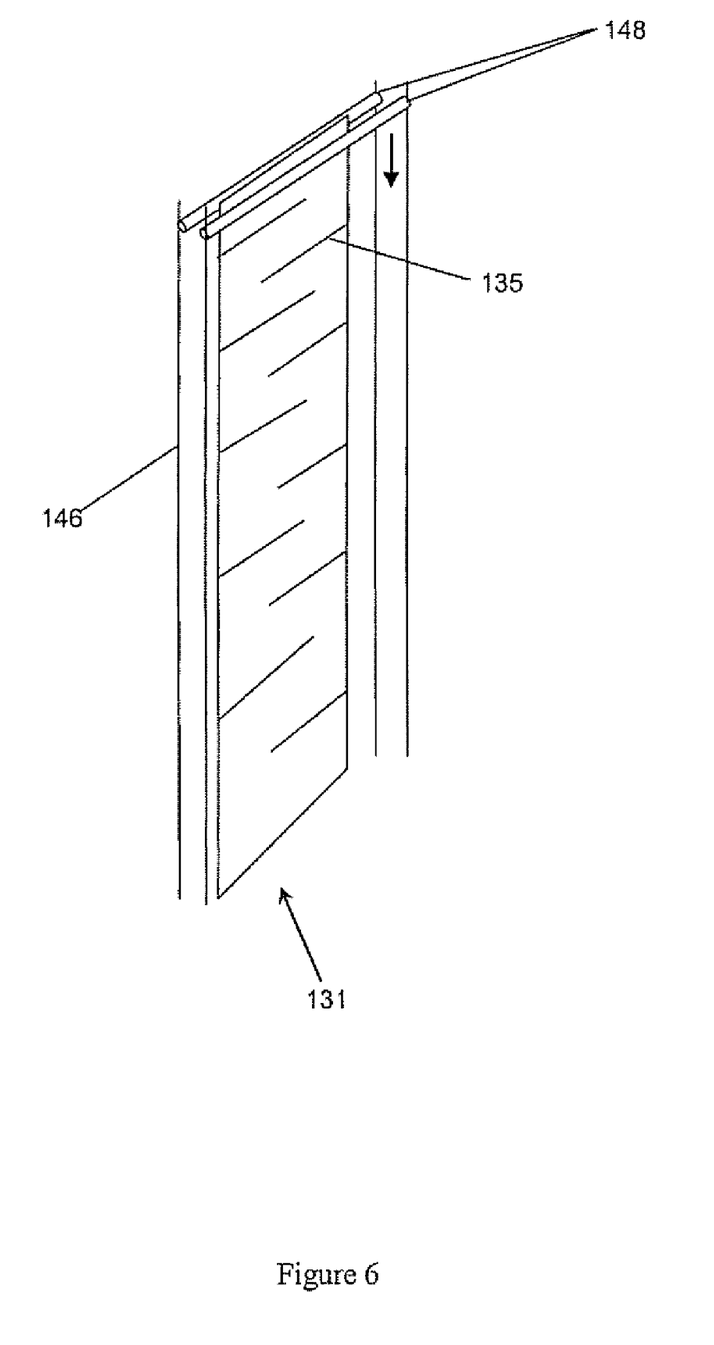
FIG. 6 illustrates a cleaning apparatus for a bioreactor.

Referring now to FIG. 6, in an additional embodiment, bioreactor 131 includes at least two cleaning members 148 to cause any algae clinging to the interior of the bioreactor 131 to drop off and flow through the bioreactor 131. In some embodiments, cleaning members 148 are elongate bars or rollers movably disposed horizontally on either face of bioreactor 131. In other words, bioreactor 131 is disposed in between cleaning members. In an embodiment, cleaning members 148 are coupled to vertical tracks 146 disposed on both sides of bioreactor 131. Cleaning members 148 may compress bioreactor 131 between each member 148 and move vertically up or down the height of bioreactor 131 to release any algae that has attached to the inner surface of bioreactor 131. Furthermore, cleaning members 148 may be coupled to vertical tracks 146 by movable screw arms such that cleaning members 148 move up and down to compress or release each bioreactor 131. Cleaning members 148 may be operated by computer control or manually.

In further embodiments, an artificial light source is provided. Although the light source preferably is natural sunlight, one or more artificial light sources may also be utilized. Examples of suitable artificial light sources are fluorescent lamps, halogen lamps, etc. In a specific embodiment, a combination of metal halogen lights and a sodium vapor light is utilized. The artificial light sources may be arranged around the one or more bioreactors 131 to provide as much light to the algae within each bioreactor 131.

Referring again to FIG. 1, in an additional embodiment, the apparatus includes an algae harvester 171. A tank outlet conduit 163 runs from the culture tank 101 to algae harvester 171. Generally, algae harvester 171 comprises a filter to strain out algae from the algae suspension. Algae harvester 171 also comprises a conveyer, which passes by a heating device to remove moisture from the algae. The conveyer runs to a collector, which is capable of straining out the dried algae.

In a further embodiment, the apparatus includes a water reclamation device or recycler 173. Water vapor is pumped from culture tank 101 to water recycler 173 via the water recycle conduit 161. In certain embodiments, the water recycler 173 includes a condenser, which condenses the water vapor. Furthermore, the water recycler 173 comprises a filtration system to purify the water before sending the recycled water back to the culture tank 101. Alternatively, water recycler 173 may comprise any device known to those of skill in the art used to purify water.

In yet another embodiment, the one or more bioreactors 131 are entirely covered by a protective shell 181. The function of the shell 181 is to prolong the life of bioreactors 131 and protect them from environmental elements such as wind and rain. In an embodiment, the protective shell 181 is a Quonset-type shell. The Quonset-shell is preferably made of a weatherproof material that is permeable to light. Examples of suitable materials include without limitation, polyethylene, polycarbonate, polyvinylchloride, polypropylene, or glass. In a further embodiment, the protective shell 181 is a greenhouse-type enclosure. In such embodiments, the heat produced within the greenhouse-type enclosure can be converted to electrical power for powering supplemental artificial light sources.

In a further embodiment, various lines such as inlet conduit 120 or outlet conduit 139 may be run deep underground to cool the culture medium and algae. Without being limited by theory, the ground may act as a natural heat sink or heat exchanger to absorb heat from the warmer fluid within the lines. Even during the hot summer months, the ground may remain cool enough to cool the culture medium and algae flowing through apparatus 100.

In an embodiment, a method for sequestering $CO_2$ comprises forcing $CO_2$-containing gas into a culture tank 101 containing a suspension of algae and water through gas jets 103. The gas jets 103 bubble the gas into the algae suspension. In an embodiment, gas jets 103 are provided gas from gas supply line 107. Preferably, ambient air is bubbled into the culture tank 101. The $CO_2$ in the gas is then dissolved in the algae suspension. Generally, the algae suspension entering the feed conduit 120 has a predetermined $CO_2$ concentration. In an embodiment, the $CO_2$ level is no more than about 5,000 ppm, alternatively no more than about 2,500 ppm, alternatively no more than about 1,000 ppm. $CO_2$ concentration beyond a certain level causes the algae suspension to become acidic, thereby stunting algae growth. The $CO_2$-enriched algae suspension is pumped from the culture tank 101 through feed conduit 120 to inlet manifold 151.

In an embodiment, culture tank 101 is located underground. Thus, pump 122 pumps the algae suspension from underground culture tank 101 to the top of the bioreactors 131 through feed conduit 120. In another embodiment, culture tank 101 is elevated at the same height as the top of bioreactors 131. In such embodiments, the algae suspension flows from culture tank into the inlet manifold 151 by gravity. Pump 122 is instead used to pump the algae suspension from outlet line 139 to culture tank 101.

Inlet manifold 151 distributes the algae suspension to the top of each vertically suspended bioreactor 131. From inlet manifold 151, the algae suspension flows down through circuitous channels 133 of bioreactors 131 also via gravity flow. As the suspension flows down through the bioreactors 131, the algae in the mixture are exposed to light, preferably natural sunlight. The algae uptakes or sequesters the $CO_2$ dissolved in the suspension and converts it into sugars and carbohydrates through the process of photosynthesis. In photosynthesis, a photon strikes a chloroplast within the organism. The chloroplast contains the compound, chlorophyll. In the presence of chlorophyll and $CO_2$, a chemical reaction takes place forming carbohydrates, sugars, and oxygen. Thus, through the natural process of photosynthesis, the algae sequester the $CO_2$ and convert it into other useful carbon compounds. The produced compounds are a source of nutrients for the algae allowing further growth and production of algae. When no light is available, the algae go through cellular respiration, converting the sugars into energy for the production of further algae. In an embodiment, about 1,000 to about 1,200 tons of $CO_2$ per hectare of land may be sequestered a year.

The flow rate of the algae suspension is dependent on the height of bioreactors 131 among other factors. In general, the flow rate of the suspension flowing through each bioreactor may range from about 1 gallon/hr to about 100 gallons/hr, preferably from about 5 gallons/hr to about 75 gallons/hr, more preferably from about 10 galloons/hr to about 50 galloons/hr. Alternatively, the flow rate of the algae suspension through the bioreactors may range from about 1 cm/s to about 50 cm/s, preferably from about 3 cm/s to about 25 cm/s, more preferably from about 5 cm to about 15 cm/s.

In one embodiment, the algae suspension exits bioreactors 131 through an outlet manifold 153 that combines the output from each bioreactor into a single outlet conduit 139, re-depositing the enriched algae into culture tank 101. In another embodiment, each bioreactor 131 has an outlet conduit, which flows directly into culture tank 101. Alternatively, each bioreactor 131 has an outlet conduit which directs the algae into the inlet of another bioreactor 131. Thus, in embodiments comprising more than one bioreactor 131, algae may be circulated or cycled through each bioreactor 131 at least once to maximize exposure of the algae to light. Ultimately, the algae from the one or more bioreactors 131 eventually return to culture tank 101 and then are continuously recirculated again and again through one or more bioreactors 131. Thus, the advantage of the continuous process is that even if some algae do not receive sufficient light in one cycle, chances are that those algae eventually will be exposed to light because of the continuous re-distribution of the algae through the one or more bioreactors 131.

In an embodiment, a gas such as carbon dioxide is introduced (e.g. bubbled) in each bioreactor 131 through gas inlet 163. The gas may be introduced from gas supply 107 or from another source such as ambient air. Any suitable gas may be introduced into bioreactor 131 through gas inlet. The gas introduced into bioreactor 131 may serve several purposes. For instance, the bubbling action of gas through the bioreactor 131 may facilitate further agitation and mixing of the algae and the culture medium within bioreactor 131. Without being limited by theory, the introduction of gas also may serve to maintain the rate of photosynthesis by the algae as the photosynthetic reaction is dependent on $CO_2$ concentration. If the $CO_2$ concentration within the bioreactor 131 drops too low, the algae may cease its photosynthesis. Moreover, introduction of $CO_2$-containing gas into bioreactor 131 via the gas inlet may provide a further means of absorbing or sequestering $CO_2$ from the ambient air.

In an embodiment, algae growth or concentration may be monitored by measuring the light level, which penetrates each bioreactor. For example, if the light level is less than about 250 footcandles, algae growth has likely reached a saturation point or density in which light cannot penetrate the innermost areas of bioreactors. In another embodiment, algae growth or concentration may be measured using methods or devices known by those of skill in the art to measure cell density (i.e. cells/mL of culture solution). For example, devices and methods such as without limitation, a Coulter Counter® or centrifugation may be used to determine cell density. Once it is determined from the light level that algae growth has reached a maximum, the algae suspension is pumped from the culture tank 101 through harvest conduit 163 to an algae harvester 171. In addition, conditions inside apparatus 100 may be monitored using any suitable type monitoring devices. Other variables that may be monitored include without limitation, pH, temperature, flow rate, and pressure.

Generally, the algae harvester 171 is used to remove and recover algae so that it can be used for other purposes. In an embodiment, algae is filtered from the algae suspension and then deposited on a conveyer belt. The conveyor belt passes through a drying chamber or a heater to dry the algae. The dried algae are then collected for future use. In some embodiments, the dried algae are used to produce oil for biodiesel. The dried algae can be used in many applications including without limitation, nutritional tablets for livestock, fuel for wood-burning stoves, and components for paper products. The filtered water is returned to culture tank 101 through recycle conduit 165. In general, the disclosed methods and apparatus are capable of reducing the $CO_2$ level in an area by an amount ranging from about 100 ppm to about 1,900 ppm.

Although the present invention and its advantages have been described in detail, it should be understood that various changes, substitutions and alterations may be made herein without departing from the scope of the invention as defined by the appended claims. Likewise, the sequential recitation of steps in the claims is not intended to require that the steps be performed sequentially, or that a particular step be completed before commencement of another step.

What is claimed is:

1. An apparatus for sequestering $CO_2$ comprising one or more bioreactors configured as a series of vertically descending, horizontal baffles,
    wherein the bioreactor has a generally rectangular shape hanging vertically, having a height measured vertically and a width measured horizontally;
    wherein the horizontal baffles form an enclosed, continuous, serpentine channel from the inlet to the outlet of the bioreactor, each channel having a cross-sectional width measured perpendicular to the bioreactor height and width, the cross-sectional width being significantly less than the bioreactor height and width such that the bioreactors have a generally planar configuration; and
    wherein the serpentine channel has a translucent wall, configured to flow a suspension containing algae in the presence of natural or artificial natural light, the serpentine channel translucent wall being made from a flexible polymeric material.

2. The apparatus of claim 1 further including a remote culture tank in fluid communication with one or more bioreactors containing a suspension of water and at least one algae, wherein said culture tank comprises a plurality of gas jets bubbling a $CO_2$-containing gas into said suspension.

3. The apparatus of claim 2 wherein the bioreactor inlet is located at the top of the one or more bioreactors, each inlet being in fluid communication with the channels and culture tank; and
    wherein the bioreactor outlet is in fluid communication with at least one other bioreactor or the remote culture tank.

4. The apparatus of claim 3 further including a pump for pumping the suspension to the inlet of the channels of one or more bioreactors from the remote culture tank.

5. The apparatus of claim 3 wherein the one or more bioreactor serpentine channels are formed by the plurality of baffles disposed substantially horizontally in the vertically downward flow of the algae suspension between the inlet and the outlet.

6. The apparatus of claim 5 wherein said plurality of baffles are arranged at an angle.

7. The apparatus of claim 6 wherein said plurality of baffles are arranged at an upward angle.

8. The apparatus of claim 6 wherein said plurality of baffles are arranged at different angles.

9. The apparatus of claim 1, wherein the one or more bioreactors translucent, serpentine channels that form a flow path alternating horizontally across each bioreactor baffle from top to bottom of each bioreactor.

10. The apparatus of claim 1, wherein the polymeric material is from the group comprising polyethylene, polypropylene, polystyrene, polyester, polyacrylic acid, or combinations thereof.

11. The apparatus of claim 1 wherein the one or more bioreactors includes a gas inlet for the bubbling of a $CO_2$-containing gas.

12. The apparatus of claim 1 wherein the channel has a plurality of vertical baffles.

13. The apparatus of claim 1, wherein the algae comprise *Chlorella*, red algae, brown algae, *Spirulina*, or combinations thereof.

14. The apparatus of claim 1, wherein the channel is no more than about 3 inches wide.

15. The apparatus of claim 1 wherein the one or more bioreactors are arranged in a matrix configuration.

16. The apparatus of claim 2, where the bottom of the channels of the one or more bioreactors includes an outlet that returns said suspension to the culture tank.

17. The apparatus of claim 2, further including an algae harvester in fluid communication with the culture tank, wherein the algae harvester comprises a filter to remove algae from the continuous flow of a suspension containing algae.

18. The apparatus of claim 2, further comprising a water recycler in fluid communication with the culture tank.

19. The apparatus of claim 1, wherein each bioreactor is disposed between at least two members, said at least two members are movably disposed horizontally on either face of each bioreactor.

20. The apparatus of claim 1 wherein the flexible polymeric material flexes to expand the cross-sectional width of the channels to compensate for different flow rates.

21. The apparatus of claim 1 the inlet and outlet of the one or more bioreactors communicates with a culture tank to form a closed system.

22. The apparatus of claim 21 wherein the culture tank is configured to culture algae prior to introduction to the bioreactor.

23. The apparatus of claim 21 wherein the culture tank includes feed inlets for nutrients.

24. The apparatus of claim 21 wherein algae continuously circulates through the bioreactors and culture tank and upon the algae reaching a predetermined concentration passes to a harvester without stopping the flow of algae through the bioreactors.

* * * * *